United States Patent [19]

Kuse et al.

[11] 4,336,456
[45] Jun. 22, 1982

[54] DEVICE FOR THE STERILIZATION OF LIQUIDS BY MEANS OF ULTRAVIOLET RAYS

[75] Inventors: Dieter Kuse, Niederrohrdorf; Heinz Wiederkehr, Brugg; Norbert Winkler, Wettingen, all of Switzerland

[73] Assignee: BBC Brown, Boveri & Company, Limited, Baden, Switzerland

[21] Appl. No.: 124,114

[22] Filed: Feb. 25, 1980

[30] Foreign Application Priority Data

May 9, 1979 [CH] Switzerland .......................... 4338/79

[51] Int. Cl.³ ............................................. G01N 21/24
[52] U.S. Cl. .................................. 250/436; 250/504 R
[58] Field of Search ............... 250/436, 437, 438, 504; 313/455, 110

[56] References Cited

U.S. PATENT DOCUMENTS 2,243,632  5/1941  Johnson .............................. 250/436
3,637,342  1/1972  Veloz .................................. 250/436
3,792,230  2/1974  Ray .................................... 250/504
4,250,391  2/1981  Bearda ............................... 250/436

Primary Examiner—Bruce C. Anderson
Attorney, Agent, or Firm—Oblon, Fisher, Spivak, McClelland & Maier

[57] ABSTRACT

A device for the sterilization of liquids by means of ultraviolet radiation whereby a low-pressure high-current mercury vapor lamp is used with a discharge tube as the radiation source wherein the cooling of the lamp is effected by means of an air flow circulating in the device and adjustment of the mercury vapor pressure by heating the cooled air in a heating device and the heating of a cecum-shaped piece of tubing with this heated air. In order to reduce the energy consumption during this heating phase, a mechanism is provided in the device in order to lead a first portion of the cooled air flow directly to the discharge tube of the lamp. A second portion of the cooled air flow, which is smaller in comparison with the first portion, is heated by the heating device and led to the cecum.

4 Claims, 2 Drawing Figures

DEVICE FOR THE STERILIZATION OF LIQUIDS BY MEANS OF ULTRAVIOLET RAYS

BACKGROUND OF THE INVENTION

1. Field of the Invention

The invention concerns a device for the sterilization of liquids by means of ultraviolet rays whereby a low-pressure high-current mercury-vapor lamp (UV-lamp) is used as the radiation source and which is provided with a cecum-shaped piece of tubing (cecum) arranged at the discharge tube such that, for the cooling of the UV-lamp, an air flow circulates through the device which is led in such a manner that the air heated at the discharge tube passes the electrode bulbs of the UV-lamp and reaches the outer wall of the piping through which the liquid flows that is to be sterilized. Moreover, the air cooled at the outer wall of the piping again returns to the UV-lamp and has a temperature which is lower than the operating temperature of the cecum such that, initially, at least part of the air reaches the cecum and the given temperature of the cecum is controlled by a heating device.

2. Description of the Prior Art

A similar device was already proposed in the Swiss Patent Application No. 6207/78 corresponding to U.S. Pat. No. 4,250,391. In the case of this device, the air flow for the cooling of the UV-lamp passes through the space around the cecum to the heated discharge tube arranged in a quartz protection tube as shown in FIG. 1.

In this instance, the circulating speed of the air flow, the temperature of the liquid to be sterilized and the heating device determine the temperature of that portion of the air flow destined for cooling of the UV-lamp. In the case of cold liquids, it might become necessary to supply a high quantity of energy to the cooled air by means of the heating device.

SUMMARY OF THE INVENTION

It is, therefore, the object of the present invention to advance the device described in Swiss Patent Application which corresponds to U.S. Pat. No. 4,250,391 in such a manner that the adjustment of the operating temperature of the cecum can be achieved without a high energy supply from the heating device even with an air flow cooled far below the operating temperature of the cecum.

This object is accomplished according to the present invention by the fact that a mechanism is provided to lead a first portion of the cooled air flow directly to the discharge tube of the UV-lamp.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein.

DETAILED DESCRIPTION OF THE PREFERRED EMBODIMENT

Figure 1:
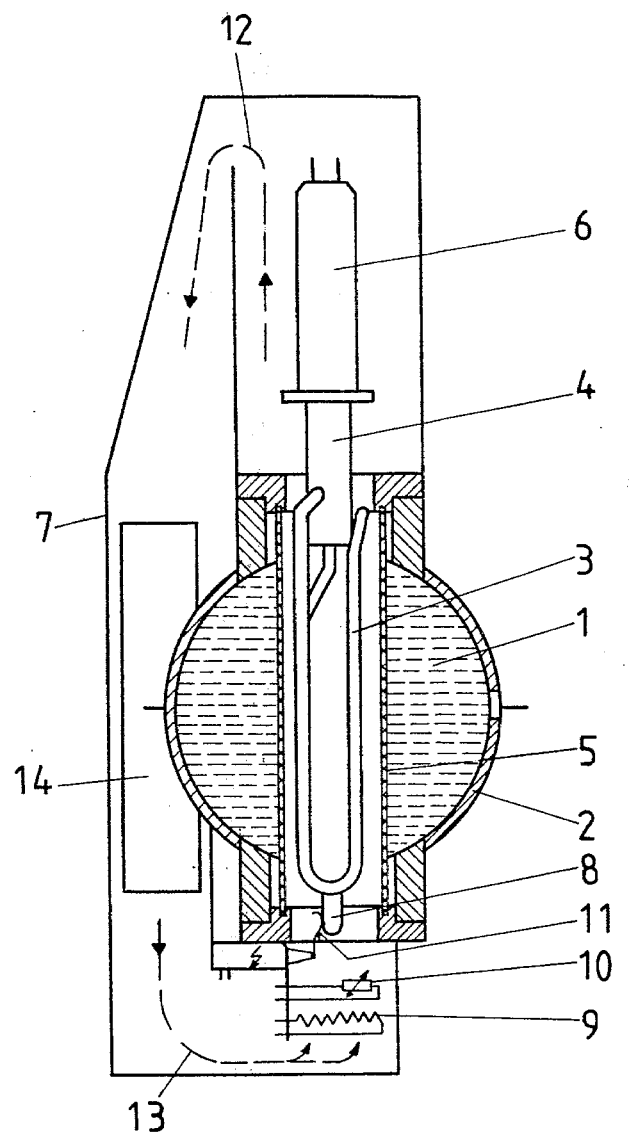
FIG. 1 shows a cross-sectional view of a prior art device.
Figure 2:
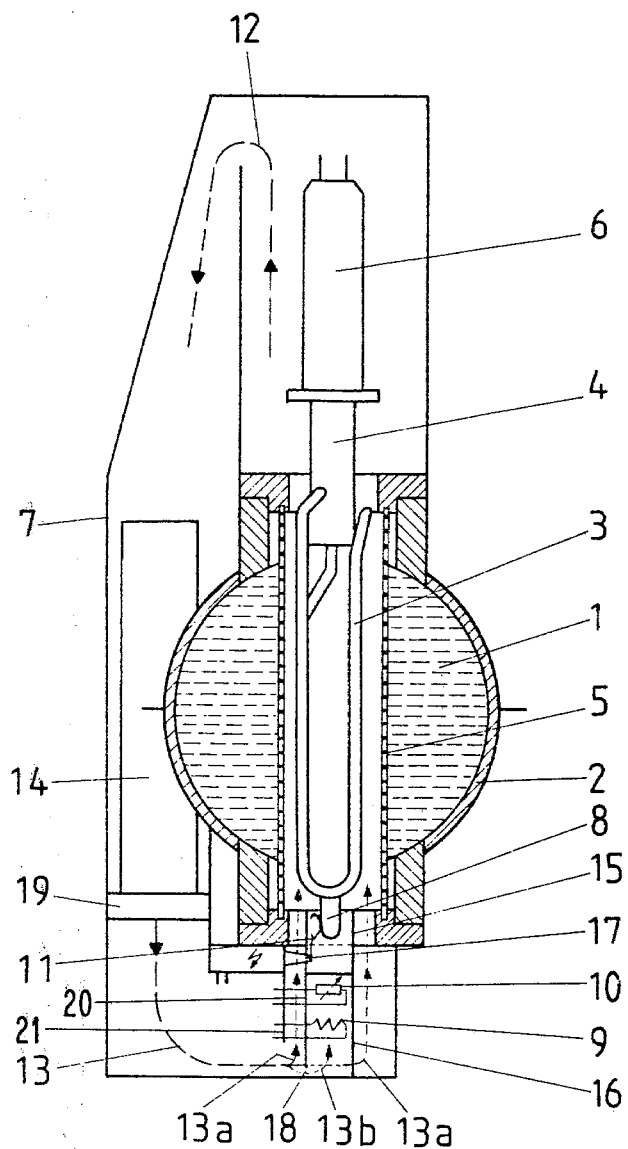
FIG. 2 shows a cross-sectional view of the preferred embodiment of the present invention.

FIG. 2 shows schematically a cross-sectional view of a sterilization device according to the invention which is similar in some respects to the prior art device of FIG. 1. The medium 1 to be sterilized flows through a piping or pipeline 2 in which, for example, a U-shaped discharge tube 3 of the UV-lamp 4 is arranged in a quartz protection tube 5. The UV-lamp 4 is placed in a continuous space for this purpose. The upper part of this space, in which electrode bulbs 6 are placed, is above or upstream of the piping 2 and is connected, through a duct 7, with the lower part of the space in which the cecum 8 is positioned and a tube 20 which opens toward the discharge tube 3 and axially surrounds the cecum.

The tube 20 includes, in the area of its open end 15, electrically insulating material, for example, of glass, and has an opening 17 to pass a high-voltage high-frequency ignition electrode 11 through it. In the area of the opposite end 16, the tube 20 has at least one additional opening 18.

The heating device 9 and the temperature sensor 10 are installed inside the tube 20 between the openings 17 and 18. The heating device 9 is controlled by a regulating device which maintains the temperature at the cecum 8 at a constant level by means of the temperature sensor 10. The connecting duct 7 is in thermal contact with the flowing medium 1 through cooling plates 14.

The mode of operation of this device is essentially based on the circulation of air inside the device. The air 12 heated by the discharge passes the electrode bulbs 6 and enters the connecting duct 7 and is then cooled at the piping 2 as well as the additional cooling plates 14.

A first portion or stream 13a of the cooled air flow 13 is led directly to the discharge tube 3 of the UV-lamp 4 along the outside of the tube 20. A second portion or stream 13b of the cooled air flow 13 enters the interior of the tube 20 through the opening 18 and is adjusted to the given temperature of the cecum 8 with the help of the heating device 9 and the temperature sensor 10. Since it is the primary task of the second portion 13b of the cooling air flow to maintain the operating temperature of the cecum 8 at a constant level, only a comparatively small amount of air 13b need flow through the inside of the tube 20.

If the device is operated in the manner represented in FIG. 2, i.e. the electrode bulbs of the UV-lamp 4 are directed towards the top and the cecum 8 is directed towards the bottom, the air circulation is thus already effected by means of convection. Additional measures, such as the introduction of an air circulating pump or of a blower, are actually not required but, at times, it is to be recommended to install a fan 19 since air circulation is accelerated by this measure and better cooling of the discharge tube 3 is effected.

It is advantageous that, with the new device, the heating appliance 9 need now only heat the second portion 13b of the cooled air flow 13 to the operating temperature of the cecum so that the heating device 9 can be of a correspondingly small size.

Since the main portion 13a of the cooled air flow 13 reaches the discharge tube 3 directly without intermediate heating device 9, the cooling effect of the air flow 13 is, furthermore, utilized to a maximum degree. It should, moreover, be emphasized that, on the basis of the air flow divided according to the invention, it is possible to install a fan 19 effecting a strong cooling in the circulating air flow 12, 13 even with the use of a small sized heating device 9.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An apparatus for sterilizing liquids by means of ultraviolet rays wherein the source of radiation used is a low-pressure high-current mercury vapor lamp which is provided with a cecum-shaped piece of tubing located on a discharge tube, comprising:

a pipeline through which said liquids flow disposed around said discharge tube;

at least one electrode bulb;

means for circulating a stream of air through the apparatus such that air travels past said at least one electrode bulb to an outer wall of the pipeline and such that air that has cooled on the outer wall of the pipeline is returned to said mercury vapor lamp at a temperature lower than the operating temperature of said cecum-shaped piece of tubing;

means for separating said stream of cooled air upstream of said cecum-shaped piece of tubing into first and second streams of cooled air such that said second stream of cooled air communicates with said cecum-shaped piece of tubing and said first stream of cooled air directly communicates with said discharge tube; and heating means positioned in said second stream of cooled air for heating said second stream of cooled air and for controlling the temperature of said cecum-shaped piece of tubing.

2. The apparatus as set forth in claim 1, said means for separating said stream of cooled air comprising first and second tubes opening towards said discharge tube such that at least one of said first and second tubes axially surrounds said cecum-shaped piece of tubing.

3. An apparatus as set forth in claim 2, further comprising electrode insulating material disposed in an open end portion of said means for separating said stream of cooled air; and a high voltage ignition electrode positioned in at least one of said first and second tubes.

4. An apparatus as set forth in claims 1 or 2 or 3, further comprising fan means for increasing circulation of said stream of air through the apparatus.

* * * * *